(12) United States Patent
Jeong et al.

(10) Patent No.: US 12,097,014 B2
(45) Date of Patent: Sep. 24, 2024

(54) BIO-SIGNAL MONITORING DEVICE

(71) Applicant: ATSENS CO., LTD., Gyeonggi-do (KR)

(72) Inventors: Jong Ook Jeong, Gyeonggi-do (KR); Jong Sung Kim, Seoul (KR); Chang Ho Lee, Gyeonggi-do (KR)

(73) Assignee: ATSENS CO., LTD., Gyeonggi-do (KR)

( * ) Notice: Subject to any disclaimer, the term of this patent is extended or adjusted under 35 U.S.C. 154(b) by 0 days.

(21) Appl. No.: 17/340,772

(22) Filed: Jun. 7, 2021

(65) Prior Publication Data

US 2022/0031174 A1 Feb. 3, 2022

(30) Foreign Application Priority Data

Jul. 28, 2020 (KR) ........................ 10-2020-0093857

(51) Int. Cl.
| | |
|---|---|
| *A61B 5/0245* | (2006.01) |
| *A61B 5/00* | (2006.01) |
| *A61B 5/01* | (2006.01) |
| *A61B 5/08* | (2006.01) |
| *A61B 5/28* | (2021.01) |
| *A61B 5/308* | (2021.01) |
| *A61B 5/318* | (2021.01) |

(52) U.S. Cl.
CPC ............. *A61B 5/0245* (2013.01); *A61B 5/01* (2013.01); *A61B 5/0816* (2013.01); *A61B 5/28* (2021.01); *A61B 5/308* (2021.01); *A61B 5/318* (2021.01); *A61B 5/6833* (2013.01); *A61B 5/7267* (2013.01); *A61B 5/7275* (2013.01); *A61B 2562/0271* (2013.01)

(58) Field of Classification Search
CPC ....... A61B 5/0245; A61B 5/01; A61B 5/0816; A61B 5/7275
See application file for complete search history.

(56) References Cited

U.S. PATENT DOCUMENTS 10,045,700 B2 8/2018 Noh et al.
10,720,044 B2 7/2020 Zdeblick et al.
(Continued)

FOREIGN PATENT DOCUMENTS

CN 208904638 U * 5/2019 ........... A61B 5/0402
JP 2009528909 8/2009
(Continued)

OTHER PUBLICATIONS

Office Action issued to corresponding Korean Application 1020200093857, issued Oct. 15, 2020.

*Primary Examiner* — Yingchuan Zhang
*Assistant Examiner* — Laura Hodge
(74) *Attorney, Agent, or Firm* — Guntin & Gust, PLC; Miyoung Shin

(57) ABSTRACT

Disclosed is a bio-signal monitoring device including an electrocardiogram detector, one or more sensor units, a controller configured to process the electrocardiogram signal or a sensing signal received from the sensor units, a connector configured to be connected to the sensor units and to transmit, to the controller, a sensing signal from the sensor units, and a communicator configured to communicate with an external electronic device. The sensing units include a breathing rate sensor, an acceleration sensor, a temperature sensor, or a combination thereof.

7 Claims, 17 Drawing Sheets

(56) References Cited

U.S. PATENT DOCUMENTS

| | | | |
|---|---|---|---|
| 2009/0093687 A1* | 4/2009 | Telfort | A61B 5/0215 600/300 |
| 2011/0066064 A1* | 3/2011 | Jangle | A61B 5/7214 600/534 |
| 2013/0009783 A1* | 1/2013 | Tran | A61B 5/01 340/669 |
| 2016/0029905 A1 | 2/2016 | Kovacs | |
| 2016/0070245 A1* | 3/2016 | Lee | A61B 5/0004 700/49 |
| 2016/0262702 A1* | 9/2016 | Cho | A61B 5/6898 |
| 2017/0076057 A1* | 3/2017 | Burton | G16H 10/60 |
| 2018/0168458 A1* | 6/2018 | Pekander | A61B 5/0809 |
| 2020/0245890 A1* | 8/2020 | Harrison | A61B 5/6803 |

FOREIGN PATENT DOCUMENTS

| | | | | |
|---|---|---|---|---|
| KR | 1020070096620 | | 10/2007 | |
| KR | 1020110094147 | | 8/2011 | |
| KR | 1020170019189 | | 2/2017 | |
| WO | WO-2005067790 A1 * | | 7/2005 | A61B 5/02405 |

* cited by examiner

BIO-SIGNAL MONITORING DEVICE

CROSS-REFERENCE TO RELATED APPLICATION

This application is based on and claims priority under 35 U.S.C. § 119 to Korean Patent Application No. 10-2020-0093857, filed on Jul. 28, 2020, in the Korean Intellectual Property Office, the disclosure of which is incorporated by reference herein in its entirety.

BACKGROUND

1. Field

The present disclosure relates to a bio-signal monitoring device.

2. Description of the Related Art

A conventional method of measuring an electrocardiogram signal among bio-signals is a Holter electrocardiometer. In order to measure a user's electrocardiogram signals, the user visits a medical institution, receives a primary diagnosis for electrocardiogram measurement, and attaches a Holter electrocardiometer for 24 hours to measure electrocardiogram signals. The user needs to visit the medical institution again and return the measuring device attached to the user. Electrocardiogram signals sensed for 24 hours are recorded in an internal memory in the Holter electrocardiometer, and the recorded electrocardiogram signals are downloaded to a PC of an analyst. The analyst may analyze downloaded electrocardiogram data using an analysis software and generate an analysis report including analysis statistics and summary information.

An analysis report generated by the analyst is delivered to a medical specialist, and the medical specialist reviews the analysis report and derives a diagnosis result.

SUMMARY

The present disclosure provides a bio-signal monitoring device and a method of monitoring bio-signals.

Additional aspects will be set forth in part in the description which follows and, in part, will be apparent from the description, or may be learned by practice of the presented embodiments of the disclosure.

According to an embodiment of the present disclosure, a bio-signal monitoring device includes an electrocardiogram detector configured to detect an electrical signal from the heart of an object and output an electrocardiogram signal, one or more sensor units including at least one of a breathing rate sensor, an acceleration sensor, and a temperature sensor, a controller configured to process the electrocardiogram signal or a sensing signal received from the one or more sensor units, a connector configured to be connected to the one or more sensor units and to transmit, to the controller, a sensing signal from the one or more sensor units, and a communicator configured to communicate with an external electronic device, wherein the controller includes a first signal analyzer configured to receive the electrocardiogram signal and generate first analysis data by analyzing the electrocardiogram signal, a second signal analyzer configured to receive a sensing signal from at least one of the breathing rate sensor, the acceleration sensor, and the temperature sensor and generate second analysis data by analyzing the sensing signal, and a signal processor configured to transmit the electrocardiogram signal or some of the sensing signals to the external electronic device according to a request signal.

In at least one variant, the electrocardiogram detector and at least one of the breathing rate sensor, the acceleration sensor, and the temperature sensor may be implemented as a patch-type device.

In another variant, the signal processor may store, in an internal memory, the electrocardiogram signal not transmitted to the external electronic device the sensing signal not transmitted to the external electronic device.

The request signal may be received from the external electronic device.

In further another variant, the signal processor is further configured to calculate a first state value corresponding to a first sensing signal of the breathing rate sensor, calculate a second state value corresponding to a second sensing signal of the acceleration sensor, and, when the first state value is identical to the second state value, store one of the first sensing signal and the second sensing signal in the internal memory.

In another variant, the bio-signal monitoring device may further include a sound sensor configured to detect a voice of the object, wherein the signal processor may be further configured to, when a health risk state of the object is detected from the first analysis data or the second analysis data, activate a function of the sound sensor to obtain the voice of the object.

In another variant, the signal processor may be further configured to determine types of sensing signals used to infer a real-time health state of the object by using a state monitoring algorithm trained with a training data set that employs electrocardiogram detection signals, sensing signals, and types of sensing signals as inputs and employs state data as outputs, and generate a control signal for activating functions of sensor units corresponding to the determined types and transmitting the control signal to the sensor units through the connector.

In another variant, the signal processor may be further configured to obtain location information of the object and determine types of sensing signals corresponding to the location information, and generate a control signal for activating functions of sensor units corresponding to the determined types and transmitting the control signal to the sensor units through the connector.

In another variant, the signal processor may be further configured to obtain a current time value and determining types of sensing signals corresponding to the current time value, and generate a control signal for activating functions of sensor units corresponding to the determined types and transmitting the control signal to the sensor units through the connector.

In another variant, the signal processor is further configured to transmit sensing signals received from activated sensor units to the external electronic device.

The at least one sensor unit is provided outside the patch-type device and further includes a connection terminal connected to a sensor unit provided outside of the patch-type device.

The connector may be designed be extendable to reach each location of the at least one sensor unit.

The electrocardiogram detector may include at least an electrode configured to contact the skin of an object and sense an electrocardiogram signal generated from the object, an electrocardiogram signal processing circuit electrically connected to the electrode and configured to generate electrocardiogram data based on a first electrical signal received from the electrode, and an electrostatic protection element whose first end is connected to an input end of the electrocardiogram signal processing circuit, wherein the breathing rate sensor may be connected to a second end of the electrostatic protection element, receive a second electrical signal from the second end of the electrostatic protection element, and output a sensing signal by measuring a capacitance of the object based on the second electrical signal.

The connector includes one or more communication ports.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 4B illustrates operations of an electrocardiogram detector and a breathing rate sensing circuit during a bio-signal processing period;

FIG. 4C illustrates operations of the electrocardiogram detector and the breathing rate sensing circuit during a capacitor sensing period; and FIG. 4D illustrates an implementation example of the breathing rate sensing circuit.

DETAILED DESCRIPTION

Figure 1:
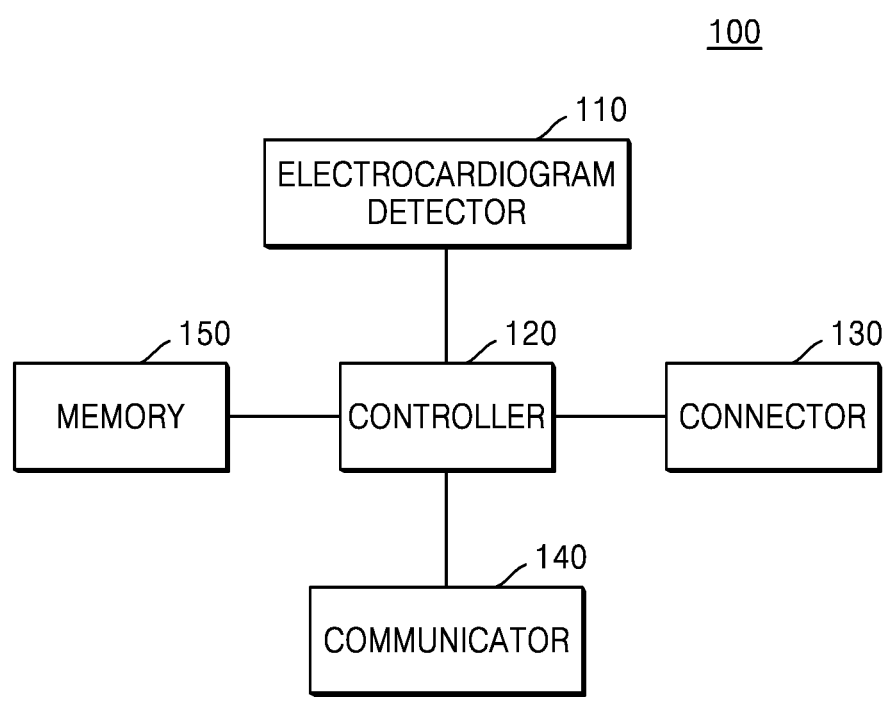
FIG. 1 is a block diagram of a bio-signal monitoring device according to a first embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, the configuration and operation of the present disclosure will be described in detail with reference to embodiments of the present disclosure shown in the accompanying drawings.

The present disclosure may include various embodiments and modifications, and embodiments thereof will be illustrated in the drawings and will be described herein in detail. The effects and features of the present disclosure and the accompanying methods thereof will become apparent from the following description of the embodiments, taken in conjunction with the accompanying drawings. However, the present disclosure is not limited to the embodiments described below, and may be embodied in various modes.

Reference will now be made in detail to embodiments, examples of which are illustrated in the accompanying drawings. In the drawings, the same elements are denoted by the same reference numerals, and a repeated explanation thereof will not be given.

In this specification, terms such as "learning" are not intended to refer to human mental processes such as educational activities, but should be interpreted as terms referring to performing machine learning through computing according to procedures.

It will be understood that although the terms "first", "second", etc. may be used herein to describe various elements, these elements should not be limited by these terms. These elements are only used to distinguish one element from another.

As used herein, the singular forms "a," "an" and "the" are intended to include the plural forms as well, unless the context clearly indicates otherwise.

It will be further understood that the terms "comprises" and/or "comprising" used herein specify the presence of stated features or components, but do not preclude the presence or addition of one or more other features or components.

Sizes of elements in the drawings may be exaggerated for convenience of explanation. In other words, since sizes and thicknesses of components in the drawings are arbitrarily illustrated for convenience of explanation, the following embodiments are not limited thereto.

When a certain embodiment may be implemented differently, a specific process order may be performed differently from the described order. For example, two consecutively described processes may be performed substantially at the same time or performed in an order opposite to the described order.

FIG. 1 is a block diagram of a bio-signal monitoring device 100 according to a first embodiment of the present disclosure.

The bio-signal monitoring device 100 may include an electrocardiogram detector 110, a controller 120, a connector 130, a communicator 140, and a memory 150.

The electrocardiogram detector 110 detects an electrical signal from the heart of an object and outputs an electrocardiogram signal. Here, the object may be a human, an animal, or a part of a human body or an animal body like a chest. However, the object is not limited thereto, and anything may be the object as long as an electrocardiogram may be detected or measured therefrom. It is important to note that the electrocardiogram detector 110 is used to measure electro-potentials from other muscle activities. Also, an electrocardiogram is a graph that records a change in potential that appears on a body surface according to mechanical activities of a heartbeat, such as contraction/expansion of a heart muscle. Here, the expression 'sensing an electrocardiogram' will be considered as being identical to 'sensing a potential' occurring on a body surface according to the heartbeat of an object. The electrocardiogram detector 110 may be implemented in the form of a patch and may be implemented in a form connected to the bio-signal monitoring device 100.

The controller 120 may receive an electrocardiogram signal from the electrocardiogram detector 110 and determine a heart state, a health state, and a health risk state of the object from the electrocardiogram detection signal. The controller 120 may receive electric signals from external sensing devices connected to the connector 130.

The controller 120 may include hardware or software components that process sensing signals of external sensing devices. When a sensing signal is received from a new sensing device, the controller 120 may additionally include a component that processes the sensing signal of the new sensing device only for the first time. The controller 120 may receive a processing-related program from a connected sensing device through wire or wireless communication. The controller 120 may receive a processing-related program from a remote device through wire or wireless communication.

External sensing devices connected to the connector 130 may include a breathing rate sensor, an acceleration sensor, a temperature sensor, a pressure sensor, a flow sensor, a magnetic sensor, an optical sensor, a taste sensor, an olfactory sensor, etc. The connector 130 may include one or more ports and be connected to one or more sensing devices. Ports may receive signals from respective sensing devices in a time division way. The connector 130 may receive sensing signals using the same number of ports as the number of connected sensing devices.

The connector 130 may further include cables extending to positions of respective sensing devices. Electrical devices may be at locations to obtain desired bio-signals using cables. The connector 130 may receive sensing signals from sensing devices and transmit the sensing signals to the controller 120, using cables implemented to be extendable. The connector 130 may be implemented as a connector for connecting various cables.

Also, the connector 130 may receive sensing signals through a wireless communication method. In detail, the connector 130 may be implemented to receive a sensing signal in a short-range wireless communication method. The short-range wireless communication methods may include a personal area network (PAN) and a body area network (BAN). For example, as shown in FIG. 9C, a temperature sensor 163 may be implemented as an optical type to transmit a temperature sensing value in a wireless method, and other sensing devices, for example, the breathing rate sensor 161, the acceleration sensor 162, and the sound sensor 165, may transmit sensing signals (sensing data) through wires. The connector 130 may include a module capable of performing a wired communication and/or a module capable of performing a wireless communication. However, the present disclosure is not limited thereto, and the connector 130 may receive a sensing signal from at least one of the breathing rate sensor 161, the acceleration sensor 162, and the sound sensor 165 through a wireless communication method. The bio-signal monitoring device 100 may receive a sensing signal from some of sensing devices and may receive no sensing signal from the remaining sensing devices, under the control of the controller 120.

The communicator 140 is a device for transmitting and receiving data to and from a remote electronic device through a communication network. The communicator 140 is a device for transmitting and receiving data through a wireless network or a wire network. The communicator 140 may transmit and receive electrocardiogram signals or data regarding an object according to a control signal of the controller 120.

The memory 150 may store data under the control of the controller 120. The memory 150 may store an electrocardiogram signal or one or more electrical signals. The memory 150 may store data received through the communicator 140.

The controller 120 may store an electrocardiogram signal in the memory 150 or transmit an electrocardiogram signal to an external electronic device through the communicator 140. The controller 120 may store an electrocardiogram signal in the memory 150 or transmit an electrocardiogram signal to an external electronic device according to an input from the external electronic device.

The controller 120 may determine a health risk state of an object in correspondence with an electrocardiogram signal or sensing signals received through the connector 130. The controller 120 may generate state values respectively corresponding to received sensing signals and determine a health risk state of an object by using the state values.

The controller 120 may analyze sensing signals and process a determined state value in association with the sensing signals. The controller 120 may process a state value for each period determined by analyzing sensing signals for each period in association with a sensing signal of a corresponding period. The controller 120 may process sensing signals of a corresponding period based on a state value for each period. The controller 120 may analyze a sensing signal of each sensor unit to generate a state value and store the sensing signal from the sensor unit in the memory 150 or transmit the sensing signal from the sensor unit to an external electric device through the communicator 140, based on the state value for each sensor unit.

In some forms, the bio-signal monitoring device 100 may contain the electrocardiogram detector 110, the controller 120, the connector 130, the communicator 140, and the memory 150, which is implemented in one house. Alternatively, the electrocardiogram detector 110, the connector 130, the communicator 140, and the memory 150 may be implemented in a housing that is separate from the controller 120 connected through electric wires. Also, the bio-signal monitoring device 100 may contain the electrocardiogram detector 110, the controller 120, the connector 130, and the communicator 140 as one device and electrically connecting the same to the memory 150. From among connectors 130 of the bio-signal monitoring device 100, a first terminal connected to the controller 120 may be provided in the bio-signal monitoring device 100, and a second terminal connected to external electrical devices may be detachably implemented. The second terminal connected to external electric devices may be extendable according to the number of connected electric devices.

The bio-signal monitoring device 100 may be implemented in the form of a patch and be attached to a desired position in the body of an object. The bio-signal monitoring device 100 may be implemented in a housing that may be coupled to other structures, such as a necklace, a belt, a wrist watch, and a band, and may be attached through an accessory of the object.

The bio-signal monitoring device 100 may implement some of the electrocardiogram detector 110, the controller 120, the connector 130, the communicator 140, and the memory 150 in the form of one patch and implement the remaining ones as detachable components.

Figure 2:
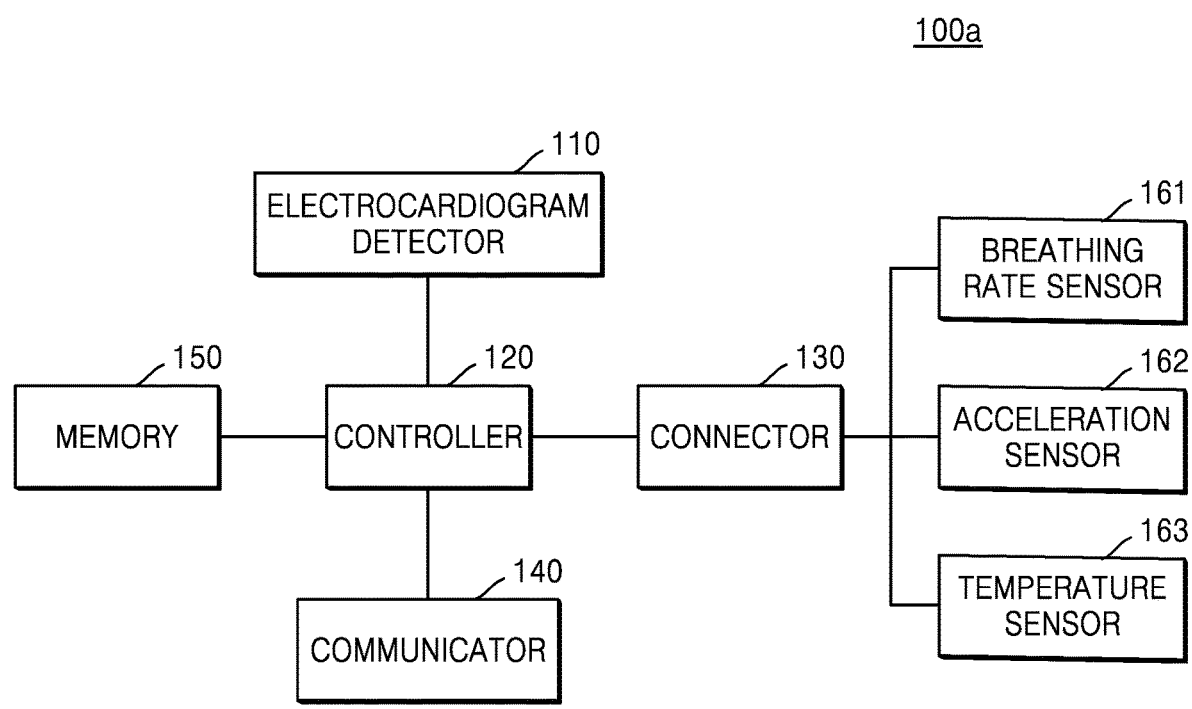
FIG. 2 is a block diagram of a bio-signal monitoring device according to a second embodiment of the present disclosure.

FIG. 2 is a block diagram of a bio-signal monitoring device 100a according to a second embodiment of the present disclosure.

The bio-signal monitoring device 100a may be a modification which further includes a breathing rate sensor 161, an acceleration sensor 162, and a temperature sensor 163 through the connector 130. The connector 130 of the bio-signal monitoring device 100a may include one or more communication terminals connected to the breathing rate sensor 161, the acceleration sensor 162, and the temperature sensor 163.

The connector 130 may be connected to some of the breathing rate sensor 161, the acceleration sensor 162, and the temperature sensor 163 under the control of the controller 120.

The controller 120 may receive sensing signals from the breathing rate sensor 161, the acceleration sensor 162, or the temperature sensor 163 and calculate a health state value of an object based on the sensing signals. The controller 120 may receive sensing signals from the breathing rate sensor 161, the acceleration sensor 162, and the temperature sensor 163, respectively, and calculate health state values of an object corresponding to the respective sensing signals.

The controller 120 may generate a control signal for one more sensor among the breathing rate sensor 161, the acceleration sensor 162, and the temperature sensor 163. The controller 120 may generate a control signal for one more sensor among the breathing rate sensor 161, the acceleration sensor 162, and the temperature sensor 163 considering a connection state with the breathing rate sensor 161, the acceleration sensor 162, or the temperature sensor 163 through the connector 130. The controller 120 may generate a control signal for activating functions of some of connected sensor units. The controller 120 may activate functions of sensor units through a control signal.

When a sensing signal is received from the breathing rate sensor 161, the acceleration sensor 162, or the temperature sensor 163 through the connector 130, the controller 120 may store the sensing signal in the memory 150. The controller 120 may transmit a sensing signal from the breathing rate sensor 161, the acceleration sensor 162, or the temperature sensor 163 to an external electronic device through the communicator 140.

The controller 120 may select some of sensing signals from the breathing rate sensor 161, the acceleration sensor 162, and the temperature sensor 163 and store the selected sensing signal(s) in the memory 150 or transmit the selected sensing signal(s) to an external electronic device through the communicator 140.

The controller 120 may generate analysis data by analyzing an electrocardiogram signal from the electrocardiogram detector 110. The analysis data may include a pulse rate of an object, an R-R interval, an interval between specific waveforms, a measurement value of a specific waveform, and the like.

Based on the analysis data, a health state value and a health risk state of the object may be determined. The controller 120 may generate analysis data by analyzing a sensing signal from the breathing rate sensor 161, the acceleration sensor 162, or the temperature sensor 163. The analysis data may include respiration rate, a value corresponding to an accelerated motion, temperature values, and a value analyzed from the values.

The controller 120 may compare a first analysis data from the breathing rate sensor 161 with a second analysis data from the acceleration sensor 162 and, when the first analysis data matches the second analysis data, may store a first sensing signal of the breathing rate sensor 161 or a second sensing signal of the acceleration sensor 162 in the memory 150 or transmit the first sensing signal or the second sensing signal to an external electronic device through the communicator 140.

The controller 120 may determine whether the first analysis data and the second analysis data match by comparing the first analysis data from the electrocardiogram signal with the second analysis data from the respiration rate sensor unit, the acceleration sensor unit, and the temperature sensor unit. When it is detected that the first analysis data and the second analysis data match, an electrocardiogram signal or a sensing signal may be stored. The coincidence of the first analysis data and the second analysis data may mean that a heart rate period from the first analysis data coincides with an analyzing period from the second analysis data. Further, the coincidence of the first analysis data and the second analysis data may be that the R-R interval value from the first analysis data matches the analyzing period from the second analysis data.

Further, the coincidence of the first analysis data and the second analysis data may be that a value from the first analysis data and a value from the second analysis data coincide.

The first or second analysis data may be data obtained by analyzing one of an electrocardiogram signal, a respiratory rate sensing signal, an acceleration sensing signal, and a temperature sensing signal.

The controller 120 may determine types of sensing signals considering at least one of a state of an object in a previous time period, current location information, and a current time value and activate functions of sensor units corresponding to determined types of sensing signals. The controller 120 may store sensing signals received from activated sensor units in the memory 150 or transmit the sensing signals to an external electronic device. A location value or a time value of an object may be received through a terminal held by the object. The controller 120 may receive real-time location values regarding an object from a terminal, thereby obtaining location information regarding the object corresponding to the received positional values.

Current location information may be set according to a periodic life style of an object. Locations where an object spends most of times may be set as 'home', 'work', or 'school'. At this time, current location information may be set considering a weekly time. For example, location values around a location value during the night may be set as "home", and location values around a location value during the night may be set as "workplace". Furthermore, locations like 'fitness center' may be additionally set. The controller 120 of the bio-signal monitoring device 100*a* may determine the type of a sensed signal considering a location value and location information corresponding to the location value.

Current time information may be considered to monitor a bio-signal according to a life cycle of an object. Because the movement of an object is small during a time period corresponding to the sleeping time of the object, the function of an acceleration sensor may be deactivated under control of the controller 120. During a time period corresponding to an exercising time of the object, the health status of the object may be monitored by activating all functions of sensors, such as a breathing rate sensor, an acceleration sensor, and a temperature sensor under the control of the controller 120. During a time period corresponding to a time in which the object is alone (e.g., a commuting time), when a health risk condition is detected, the function of a sound sensor may be activated under the control of the controller 120 to detect the voice of the object.

The controller 120 may be operated in one of a first operation mode for sensing an electrocardiogram detection signal and a breathing rate sensing signal, a second operation mode for sensing an electrocardiogram detection signal and an acceleration sensing signal, and a third operation mode for sensing an electrocardiogram detection signal, a breathing rate sensing signal, and an acceleration sensing signal. A temperature sensing signal may be successively sensed, but may also be sensed periodically or at a particular point in time.

In the first operation mode, the second operation mode, and the third operation mode, the controller 120 may sense at least one of a breathing rate sensing signal and an acceleration sensing signal at a second frequency while successively sensing an electrocardiogram detection signal at a first frequency. In the case of sensing both a breathing rate sensing signal and an acceleration sensing signal, the controller 120 may allocate different frequencies for sensing the breathing rate sensing signal and the acceleration sensing signal. Temperature sensing and sound sensing may be performed at particular time points under the control of the controller 120.

Figure 10A:
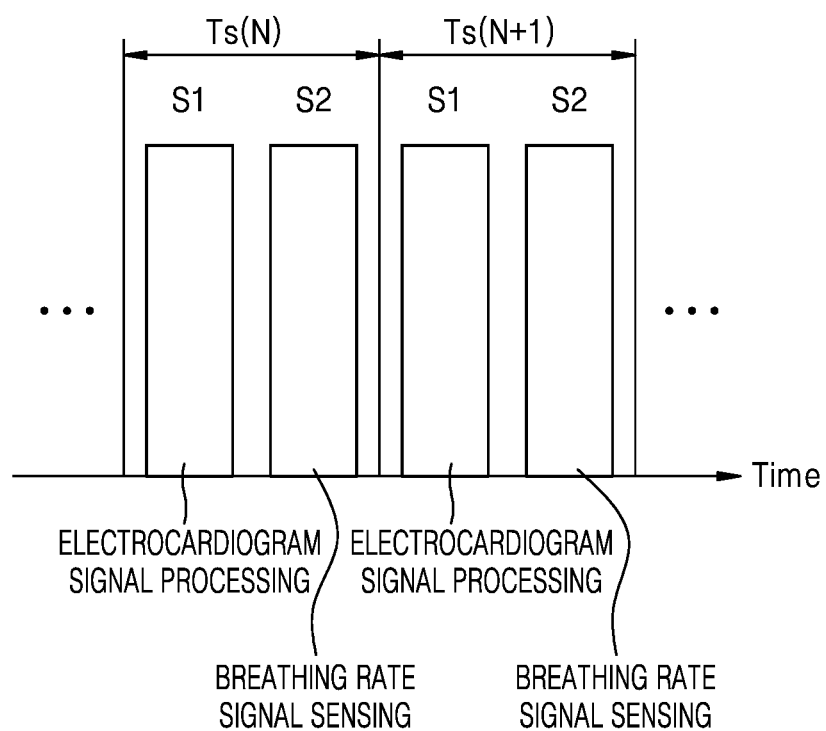
FIG. 10A is a timing diagram showing first method of operating a bio-signal monitoring device according to example embodiments of the present disclosure.

In the first operation mode, while electrocardiogram sensing is performed in an electrocardiogram sensing period (S1 of FIG. 10A) according to the timing diagram of FIG. 10A, breathing rate sensing may be performed in a breathing rate sensing period (S2 of FIG. 10A). In the third operation mode, electrocardiogram sensing, breathing rate sensing, and acceleration sensing may be performed respectively in periods S1', S2', and S3' according to the timing diagram of FIG. 10B, and temperature sensing or sound sensing may be performed in a period S4'. Temperature sensing or sound sensing may be skipped without being performed in every sampling period.

The controller 120 may be operated in one of first to third operation modes considering current location information or current time information. The controller 120 may set the operation mode to the first operation mode at 'home' and during 'sleeping time' and set the operation mode to the second operation mode at 'home' and during 'non-sleeping time'. The controller 120 may set the operation mode to the third operation mode at 'fitness center' or 'exercising time'.

The controller 120 may be operated in one of the first to third operation modes considering a health risk state and a health state that are previously generated. The health status of the object may be monitored by memorizing a location and a time of a previous health risk condition and setting the controller 120 to the third operation mode at the corresponding location and time.

Figure 3:
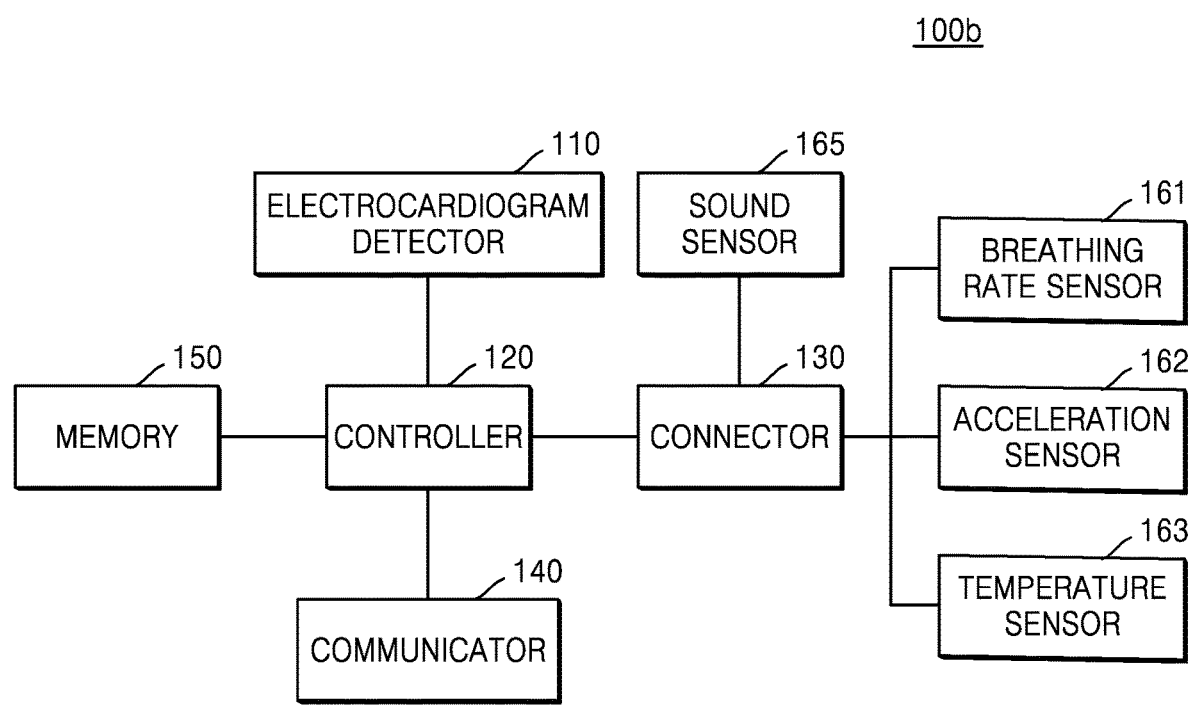
FIG. 3 is a block diagram of a bio-signal monitoring device according to a third embodiment of the present disclosure.

FIG. 3 is a block diagram of a bio-signal monitoring device 100*b* according to a third embodiment of the present disclosure.

The bio-signal monitoring device 100*b* may further include a sound sensor 165 connected to the connector 130.

The bio-signal monitoring device 100*b* may additionally activate the function of the sound sensor 165 by using a result of analyzing an electrocardiogram detection signal or a sensing signal and obtain sound through the sound sensor 165.

The controller 120 may activate the function of the sound sensor 165 considering at least one of a health risk state of an object in a previous time period, current location information, and current time value and obtain sound through the sound sensor 165.

The controller 120 may activate the function of the sound sensor 165 according to an input from an external device and obtain sound through the sound sensor 165.

The controller 120 may activate the function of the sound sensor 165 considering a condition received from an external device (including a health risk state of an object, current location information, and current time value) and obtain sound through the sound sensor 165. The controller 120 may memorize a location and a time of a previous health risk state and activate the function of the sound sensor 165 so as to obtain sound in a period of the corresponding location and time.

The sound sensor 165 may be connected to the connector 130 through an electric wire like a cable that may be at a position where a desired biometric sound is detected and may detect the biometric sound (heart sound, breath sound, pulse sound, blood vessel sound, etc.) of the object. The controller 120 may determine a health state and a health risk state of the object considering a biometric sound received from the sound sensor 165, an electrocardiogram detection signal, and a sensing signal.

The controller 120 may activate the function of the sound sensor 165 when a health risk state of the object is detected from an electrocardiogram detection signal or a sensing signal. When a health risk state of the object is detected from an electrocardiogram signal or a sensing signal, the controller 120 may activate the function of the sound sensor 165 for a set period of time and obtain ambient sound and voice of the object.

The controller 120 may determine whether the first analysis data and the second analysis data match by comparing the first analysis data from the electrocardiogram signal with the second analysis data from the respiration rate sensor, the acceleration sensor, the temperature sensor or the sound sensor. When it is detected that the first analysis data and the second analysis data match, an electrocardiogram signal or a sensing signal may be stored. The coincidence of the first analysis data and the second analysis data may mean that to heart rate period from the first analysis data coincides with an analyzing period from the second analysis data. Further, the coincidence of the first analysis data and the second analysis data may be that the R-R interval value from the first analysis data matches the analyzing period from the second analysis data.

Further, the coincidence of the first analysis data and the second analysis data may be that a value from the first analysis data and a value from the second analysis data coincide.

The first or second analysis data may be data obtained by analyzing one of an electrocardiogram signal, a respiratory rate sensing signal, an acceleration sensing signal, a temperature sensing signal or sound sensing signal.

Figure 4A:
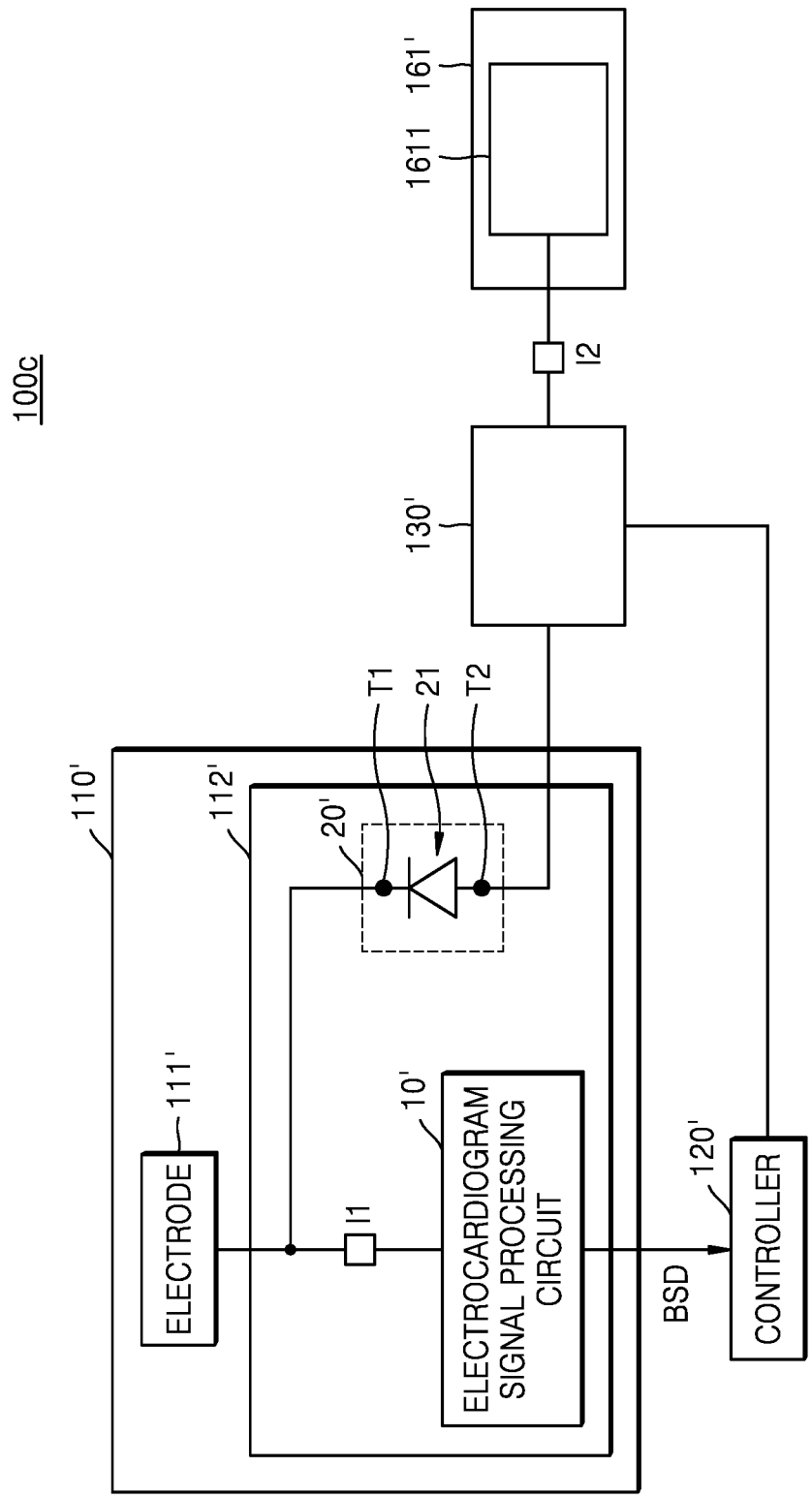
FIG. 4A is a block diagram of a bio-signal monitoring device according to a fourth embodiment of the present disclosure.
Figure 4B:
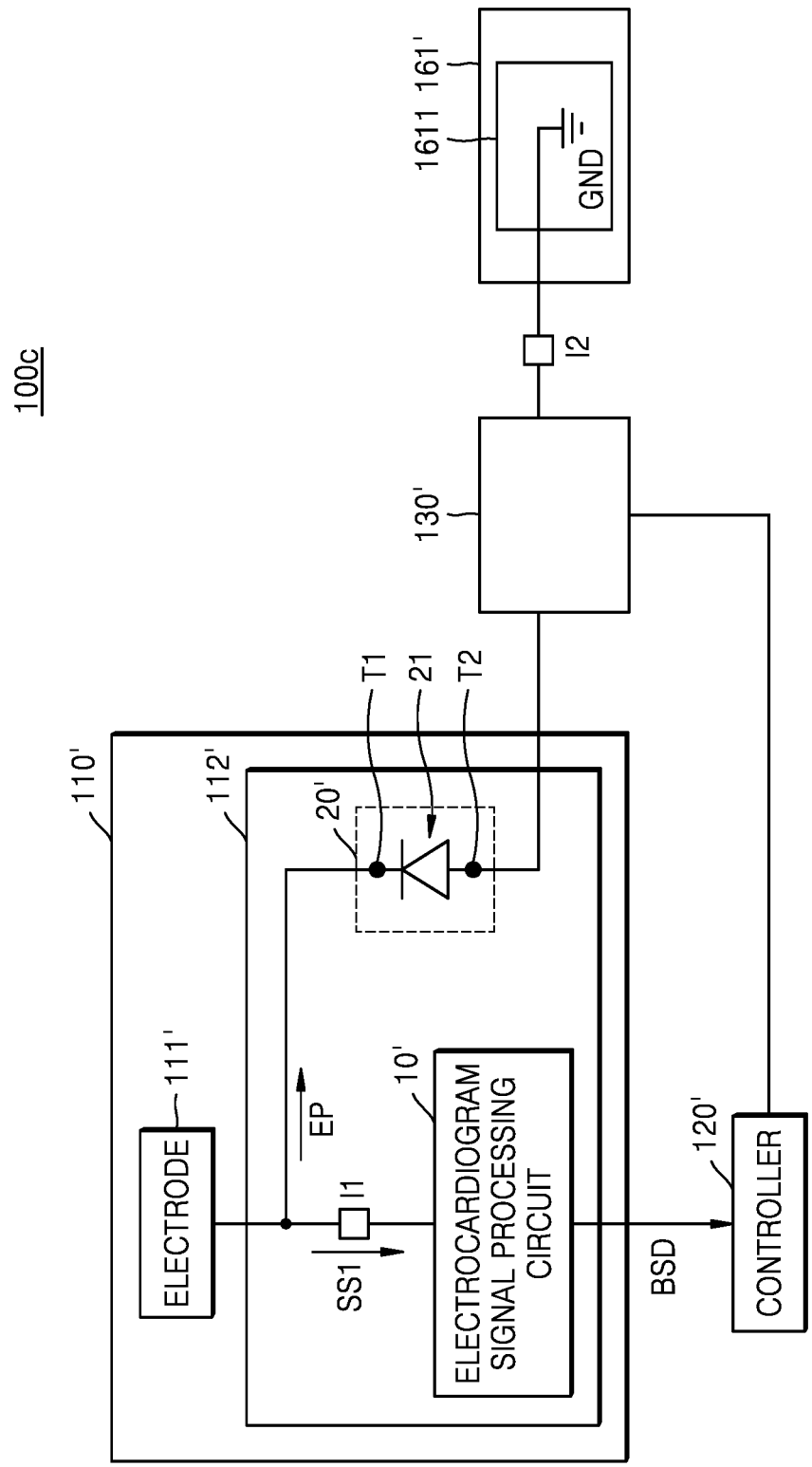
FIGS. 4B, 4C, and 4D are diagrams showing electrocardiogram signal sensing and breathing rate sensing performed in the bio-signal monitoring device of FIG. 4A, where.
Figure 4C:
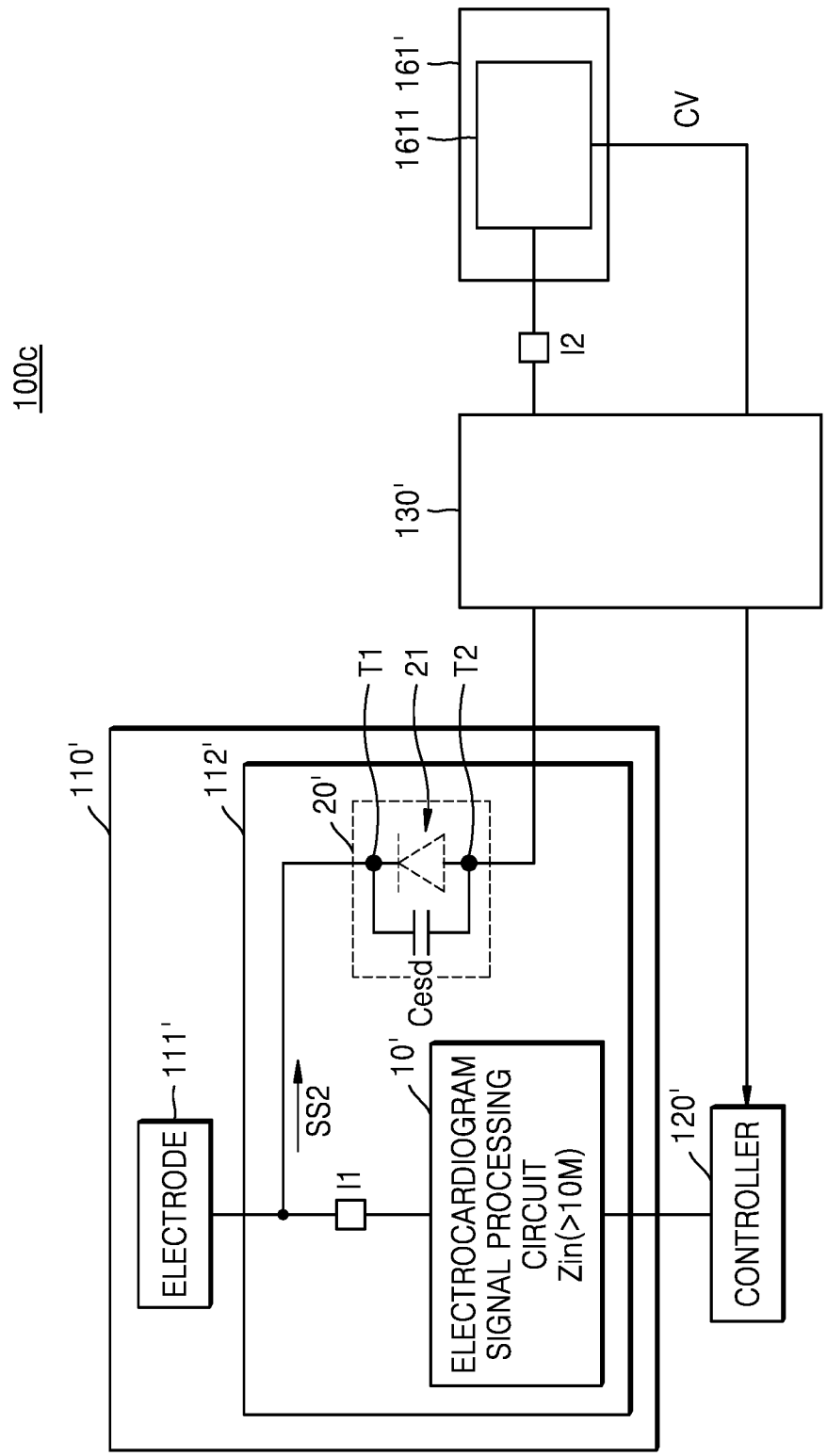
Figure 4D:
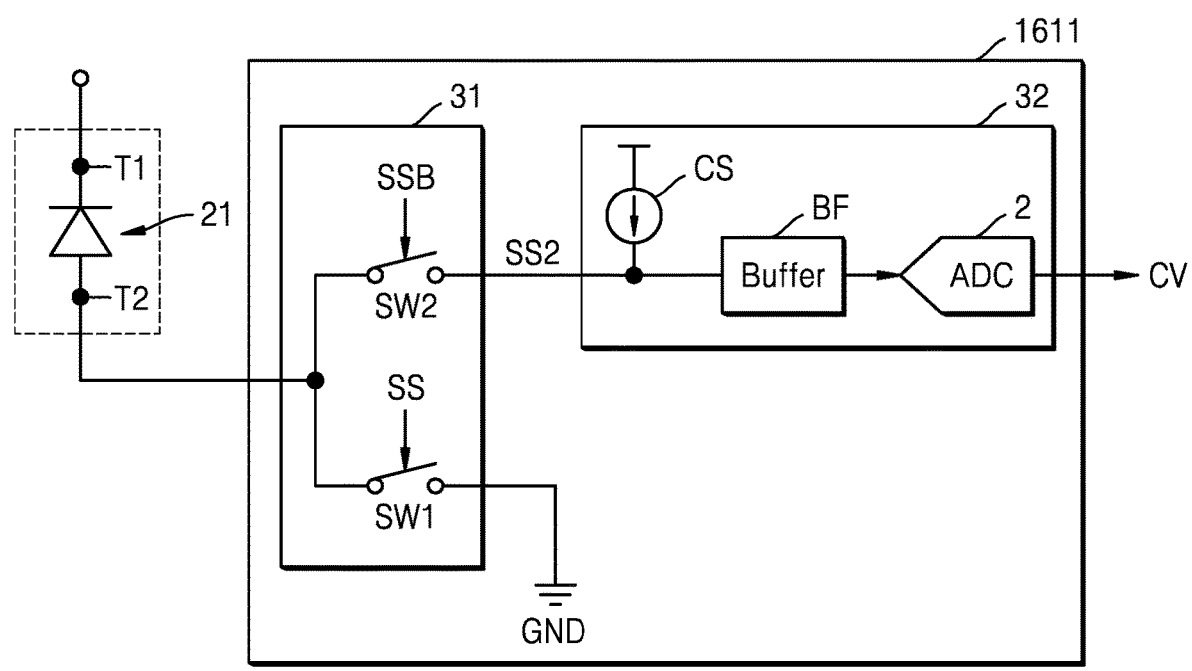

FIG. 4A is a block diagram of a bio-signal monitoring device according to a fourth embodiment of the present disclosure, and FIGS. 4B, 4C, and 4D are diagrams showing electrocardiogram signal sensing and breathing rate sensing performed in the bio-signal monitoring device of FIG. 4A.

Referring to FIG. 4A, the electrocardiogram detector 110' may include an electrode 111' and an analog front end 112', and the analog front end 112' may include an electrocardiogram signal processing circuit 10' and an electrostatic protection circuit 20'.

The electrode 111', e.g., an ECG electrode, is an electrode for measuring an electrocardiogram and may sense an electrocardiogram signal by inducing an active electropotential generated at the myocardium according to the heartbeat at the body surface.

The electrocardiogram signal processing circuit 10' may generate an electrocardiogram detection signal BSD by receiving an electrocardiogram signal through the electrode 111', amplifying the electrocardiogram signal, and analog-to-digital converting the t electrocardiogram signal. As a result, the electrocardiogram detection signal BSD may be obtained. An input end I1 of the electrocardiogram signal processing circuit 10' may be electrically connected to the electrode 111' and an electrocardiogram detection signal may be received from the electrode 111'.

The electrostatic protection circuit 20' may protect the electrocardiogram signal processing circuit 10' from being damaged even when static electricity or an overvoltage is applied to the input end I1 of the electrocardiogram signal processing circuit 10'. The electrostatic protection circuit 20' may include an electrostatic protection element 21. A first end T1 of the electrostatic protection element 21 may be connected to the input end I1 of the electrocardiogram signal processing circuit 10', and a second end T2 of the electrostatic protection element 21 may be connected to an input end I2 of a breathing rate sensor 161' through the connector 130. The second end T2 of the electrostatic protection element 21 may be grounded through a breathing rate sensing circuit 1611, as shown in FIG. 4B. In other words, a ground voltage GND may be applied to the second end T2 of the electrostatic protection element 21.

The electrostatic protection element 21 (also referred to as an electrostatic discharge protection element) is switched to a conductive state when a voltage between two ends T1 and T2 is increased above a predetermined high voltage, and thus a discharge path may be formed between the first end T1 (e.g., a cathode of a diode) and the second end T2 (e.g., an anode of a diode). Therefore, the voltage between the two ends T1 and T2 may be maintained as a constant voltage. The electrostatic protection element 21 may be implemented as a diode, e.g., a diode or a Zener diode. However, the present disclosure is not limited thereto, and the electrostatic protection element 21 may be implemented as various other types of devices like a varistor.

Meanwhile, when the voltage between the two ends T1 and T2 of the electrostatic protection element 21 is less than the predetermined high voltage, the electrostatic protection element 21 may be equivalently expressed as a capacitor (a first capacitor Cesd of FIG. 4C). The breathing rate sensing circuit 1611 connected to the second end T2 of the electrostatic protection element 21 may measure a capacitance of a capacitor formed by an object OBJ based on a signal received from the electrostatic protection element 21.

The breathing rate sensing circuit 1611 may ground the electrostatic protection element 21, but, during a breathing rate sensing period, a capacitance value CV may be generated by receiving a signal from the second end T2 of the electrostatic protection element 21. The breathing rate sensing circuit 1611 may amplify a received signal and perform analog-to-digital conversion thereon to generate the capacitance value CV representing a capacitance due to the object OBJ. When the electrode 111' is separated from the object OBJ, the capacitance value CV may be reduced as compared to the capacitance value CV while the electrode 111' is contacting the object OBJ. A sensing value of a breathing rate may be calculated based on the capacitance value CV generated by the breathing rate sensing circuit 1611.

Referring to FIG. 4B, during a bio-signal processing period S1, the electrocardiogram signal processing circuit 10' may receive a bio-signal (e.g., a first signal (also referred to as a first sensing signal) SS1) from the electrode 111' and generate the electrocardiogram detection signal data BSD by processing the first signal SS1. At this time, the breathing rate sensing circuit 1611 may ground the second end T2 of the electrostatic protection element 21, and the electrostatic protection element 21 may protect the electrocardiogram signal processing circuit 10' by forming a discharge path EP when a high voltage or an over voltage is applied to the electrocardiogram signal processing circuit 10'.

Referring to FIG. 4C, during a breathing rate sensing period S2 (shown in FIG. 10A), the breathing rate sensing circuit 1611 may generate the capacitance value CV by processing a signal (e.g., a second signal (also referred to as a second sensing signal) SS2) received from the electrostatic protection element 21. In this case, the electrocardiogram signal processing circuit 10' does not operate, and an input impedance Zin of the electrocardiogram signal processing circuit 10' may be very high. For example, the input impedance Zin may be about 10 mega ohms (MΩ) or higher. Therefore, equivalently, it may be seen as that a capacitor Cbd (hereinafter referred to as a first capacitor) due to the electrode 111' and the object OBJ and a capacitor Cesd (hereinafter referred to as a second capacitor) due to the electrostatic protection element 21 are connected in series to the input end I2 of the breathing rate sensing circuit 1611. Therefore, the breathing rate sensing circuit 1611 may generate the capacitance value CV based on the second signal SS2 received through the input end I2.

The capacitance value CV may represent capacitance according to the series connection of the first capacitor Cbd and the second capacitor Cesd. However, the capacitance of the second capacitor Cesd may be constant, and the capacitance of the first capacitor Cbd may vary according to a contact state between the object OBJ and the electrode 111'. Therefore, it may be considered that the capacitance value CV represents a capacitance related to the first capacitor Cbd. As a distance between the object OBJ and the electrode 111' increases, the capacitance of the first capacitor Cbd may decrease, and thus the capacitance value CV may decrease. As described above with reference to FIGS. 4B to 4C, the electrocardiogram signal processing circuit 10' and the breathing rate sensing circuit 1611 may process signals SS1 and SS2 alternately received during a sampling period, thereby generating a sensing signal based on the electrocardiogram signal data BSD and the capacitance value CV.

FIG. 4D is a diagram schematically showing an implementation example of a breathing rate sensing circuit according to an example embodiment of the present disclosure. For convenience of explanation, the electrostatic protection element 21 will be shown together.

Referring to FIG. 4D, the breathing rate sensing circuit 1611 may include a switching unit 31 and a sensing circuit 32, and the sensing circuit 32 may include a current-voltage converter 1 and an analog-digital converter 2.

The switching unit 31 may ground the second end T2 of the electrostatic protection element 21 or connect the second end T2 to the sensing circuit 32. The switching unit 31 may be implemented as a multiplexer including a first switch SW1 and a second switch SW2, and the first switch SW1 and the second switch SW2 may operate in a complementary manner based on a switching signal SS and a complementary switching signal SSB having complementary active levels.

For example, when a bio-signal monitoring device (100c of FIG. 4A) performs bio-signal processing S1, the first switch SW1 may be turned on in response to an active level of the switching signal SS (e.g., logic high) and ground the second end T2 of the electrostatic protection element 21. In other words, a ground voltage GND may be applied to the second end T2 of the electrostatic protection element 21. At this time, the second switch SW2 may be turned off in response to an inactive level of the complementary switching signal SSB (e.g., logic low).

When the bio-signal monitoring device (100c of FIG. 4A) performs breathing rate sensing S2, the second switch SW2 may be turned on in response to an active level of the complementary switching signal SSB (e.g., logic high) and connect the second end T2 of the electrostatic protection element 21 to the sensing circuit 32. In other words, the second switch SW2 may provide the second signal SS2 received from the electrostatic protection element 21 to the sensing circuit 32. At this time, the first switch SW1 may be turned off in response to an inactive level of the switching signal SS (e.g., logic low).

The current-voltage converter 1 may include a current source CS and a buffer BF. A voltage is generated based on the current source CS, and the voltage may vary according to the second signal SS2 indicating capacitance. The buffer BF may amplify and output a voltage. The analog-digital converter 2 may convert a voltage received from the amplifier 1 into a digital value and output the digital value as the capacitance value CV.

The bio-signal monitoring device (100c of FIG. 4A) may determine state values such as a breathing rate based on the capacitance value CV received from the breathing rate sensing circuit 1611 and, based on a result of the determination, the bio-signal monitoring device (100c of FIG. 4A) may be controlled.

Figure 5:
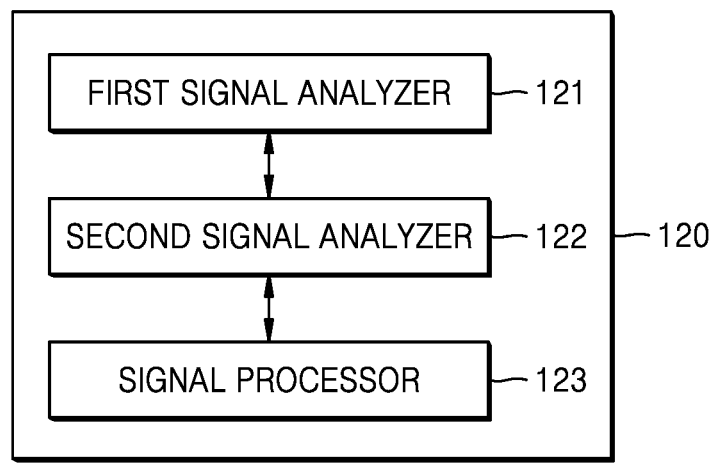
FIG. 5 is a block diagram of a controller.

FIG. 5 is a block diagram illustrating one form of a controller 120. The controller 120 may include a first signal analyzer 121, a second signal analyzer 122, and a signal processor 123. The first signal analyzer 121 may receive an electrocardiogram signal from the electrocardiogram detector 110 and generate first analysis data corresponding to the electrocardiogram signal.

The second signal analyzer 122 may receive a sensing signal from at least one of the breathing rate sensor 161, the acceleration sensor 162, and the temperature sensor 163 and generate second analysis data corresponding to the sensing signal. The second analysis data may determine an object's blood pressure, damage to one of blood vessels, brain, heart, lung, bone joints, jaw, mouth, nose, throat, veins, or arteries, or other problems related thereto.

The second signal analyzer 122 may obtain sound data from the sound sensor 165. The second signal analyzer 122 may receive heart sound, respiratory sound, pulse sound, blood vessel sound, etc. from the sound sensor 165, compare an obtained sound with an index sound of a corresponding organ of the object, and generate analysis data regarding the obtained sound.

The second signal analyzer 122 may obtain the voice of the object from the sound sensor 165. It may be determined whether a sound from the sound sensor 165 is a voice.

The signal processor 123 may determine health states like a respiration rate, arrhythmia, bradycardia or tachycardia, blood pressure, blood sugar, joint abnormalities, heart diseases, bronchitis, and risk of myocardial infarction and health risk states of the object based on the first analysis data or the second analysis data.

When the sound from the sound sensor 165 is a voice, the signal processor 123 may store sound data in the memory 150 or transmit the sound data to an external electronic device.

Figure 6:
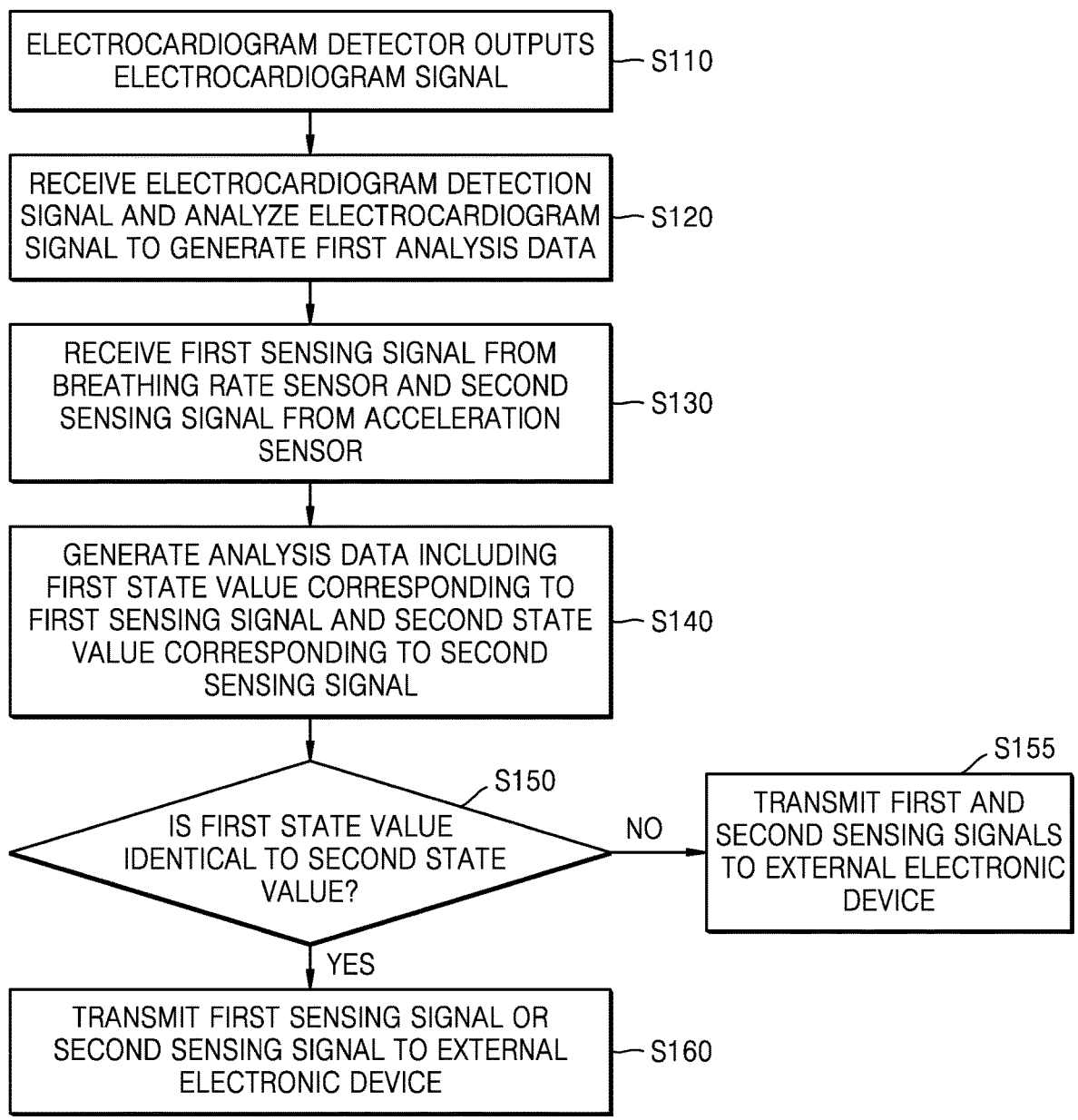
FIG. 6 is a flowchart of a first method of monitoring bio-signals according to example embodiments of the present disclosure.
Figure 7:
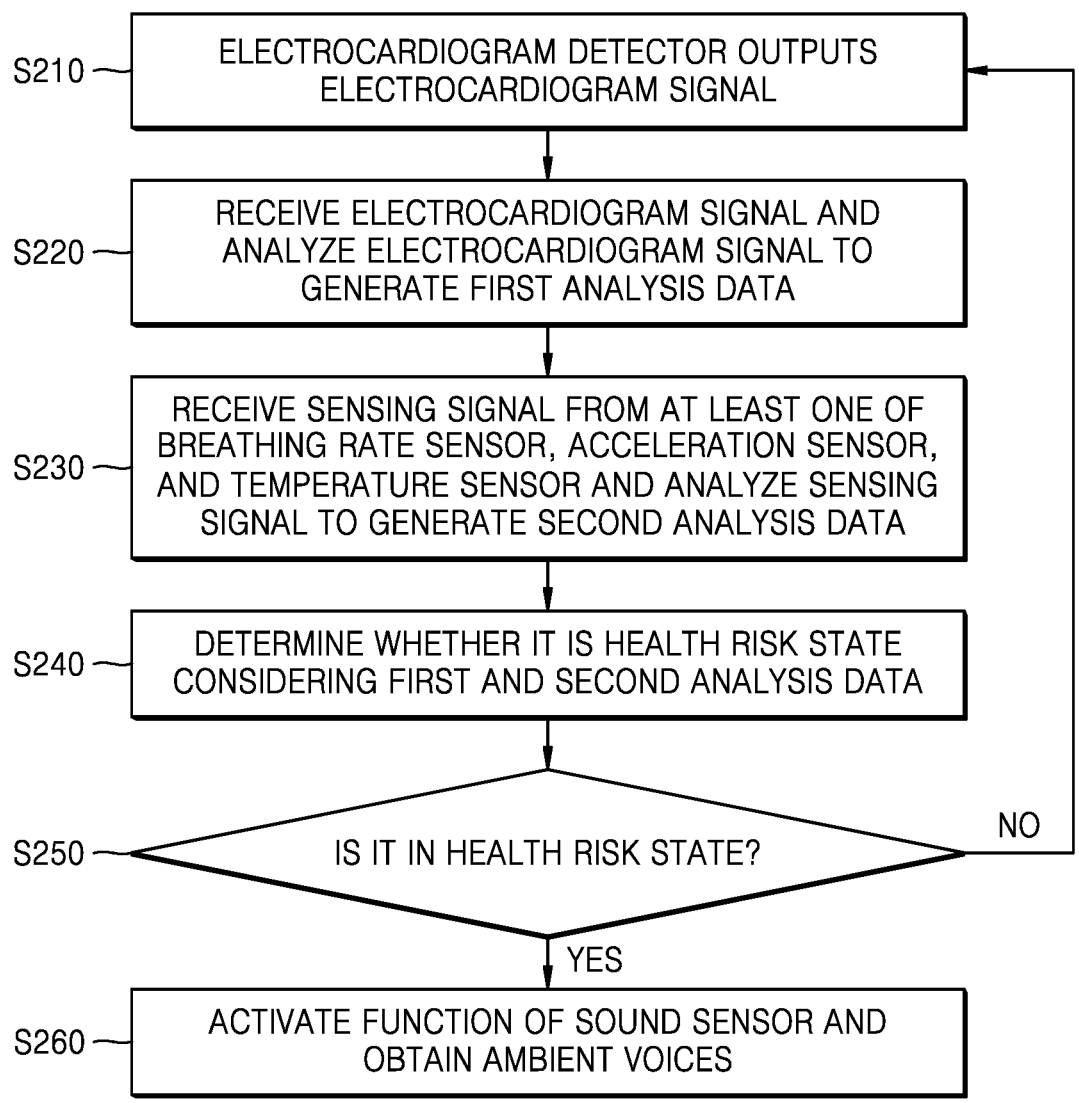
FIG. 7 is a flowchart of a second method of monitoring bio-signals according to example embodiments of the present disclosure.
Figure 8:
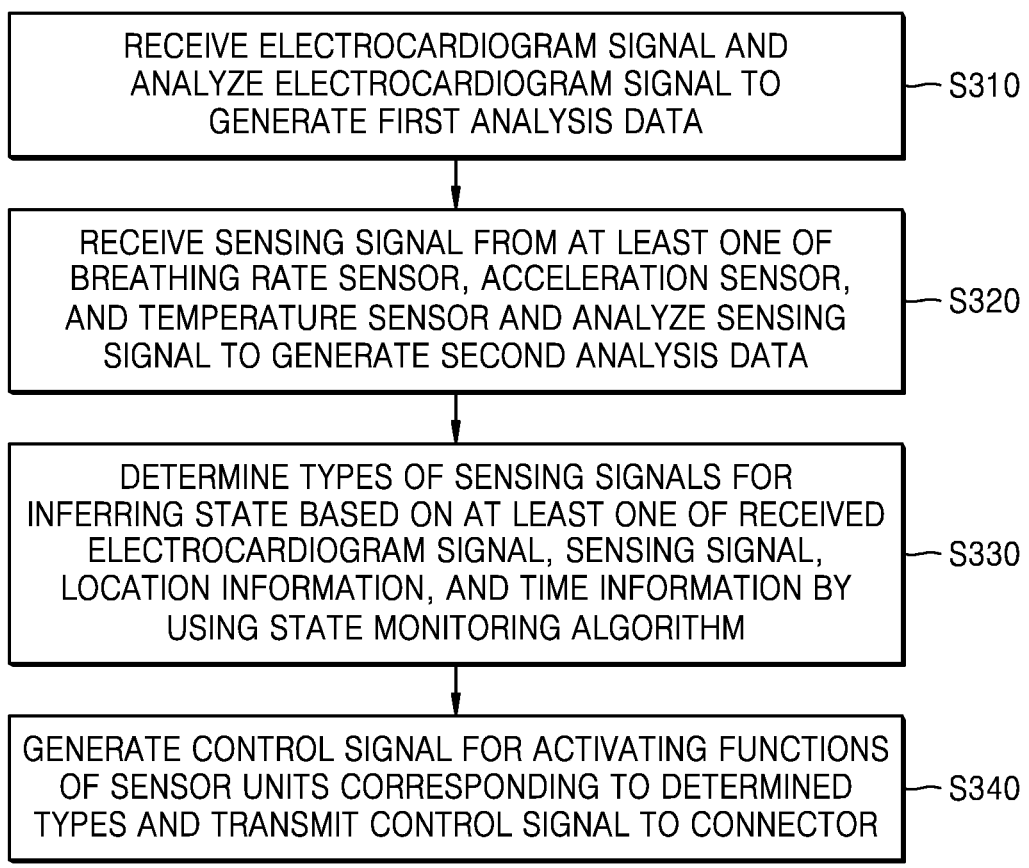
FIG. 8 is a flowchart of a third method of monitoring bio-signals according to example embodiments of the present disclosure.

FIGS. 6 through 8 are flowcharts of a method of monitoring bio-signals according to an example embodiment of the present disclosure. FIG. 6 is a flowchart of a first method of monitoring bio-signals according to example embodiments of the present disclosure. FIG. 7 is a flowchart of a second method of monitoring bio-signals according to example embodiments of the present disclosure. FIG. 8 is a flowchart of a third method of monitoring bio-signals according to example embodiments of the present disclosure.

In operation S110, in the bio-signal monitoring device 100a, 100b, or 100c, an electrocardiogram detector may output an electrocardiogram detection signal.

In operation S120, the bio-signal monitoring device 100a, 100b, or 100c may generate first analysis data by receiving an electrocardiogram detection signal and analyzing the electrocardiogram detection signal.

In operation S130, the bio-signal monitoring device 100a, 100b, or 100c may receive a first sensing signal from the breathing rate sensor 161 and a second sensing signal from the acceleration sensor 162. In operation S140, the bio-signal monitoring device 100a, 100b, or 100c may generate analysis data including a first state value corresponding to the first sensing signal and a second state value corresponding to the second sensing signal.

In operation S150, the bio-signal monitoring device 100a, 100b, or 100c may determine whether the first state value is identical to the second state value.

In operation S160, when the first state value is identical to the second state value, the bio-signal monitoring device 100a, 100b, or 100c may transmit the first sensing signal or the second sensing signal to an external electronic device. In operation S155, when the first state value is not identical to the second state value, the bio-signal monitoring device 100a, 100b, or 100c may transmit both the first sensing signal and the second sensing signal to an external electronic device.

Referring to FIG. 7, in operation S210, in the bio-signal monitoring device 100a, 100b, or 100c, an electrocardiogram detector may output an electrocardiogram detection signal. In operation S220, the bio-signal monitoring device 100a, 100b, or 100c may generate first analysis data by receiving the electrocardiogram detection signal and analyzing the electrocardiogram detection signal. In operation S230, the bio-signal monitoring device 100a, 100b, or 100c may generate second analysis data by receiving a sensing signal from at least one of a breathing rate sensor, an acceleration sensor, and a temperature sensor, and analyzing the sensing signal.

In operation S240, the bio-signal monitoring device 100a, 100b, or 100c may determine whether an object is in a health risk state considering first and second analysis data. In operations S250 and S260, when it is determined that the object is in a health risk state, the bio-signal monitoring device 100a, 100b, or 100c may activate a function of a sound sensor to obtain ambient voice.

As shown in FIG. 8, in operation S310, the bio-signal monitoring device 100a, 100b, or 100c may generate first analysis data by receiving an electrocardiogram detection signal and analyzing the electrocardiogram detection signal. In operation S320, the bio-signal monitoring device 100a, 100b, or 100c may generate second analysis data by receiving a sensing signal from at least one of a breathing rate sensor, an acceleration sensor, and a temperature sensor, and analyzing the sensing signal. In operation S330, the bio-signal monitoring device 100a, 100b, or 100c may use a state monitoring algorithm to determine types of sensing signals used to infer a health state based on at least one of a received electrocardiogram detection signal, a received sensing signal, location information, and time information.

In operation S340, the bio-signal monitoring device 100a, 100b, or 100c may generate control signals for activating functions of sensor units corresponding to the determined types and transmit the control signals to a connector.

Figure 9A:
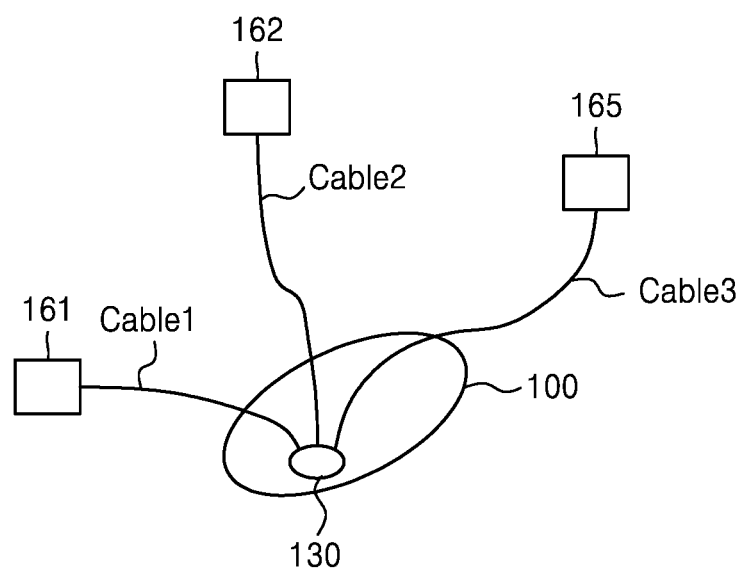
FIG. 9A is a diagram showing an implementation example of bio-signal monitoring devices according to an example embodiment of the present disclosure.

FIG. 9A is a diagram showing an implementation example of bio-signal monitoring devices 100a, 100b, and 100c according to an example embodiment of the present disclosure.

As shown in FIG. 9A, the breathing rate sensor 161, the acceleration sensor 162, and the sound sensor 165 may be connected to the bio-signal monitoring device 100 through cables cable1, cable2, and cable3 that are connected to the connector 130. First ends of the cables cable1, cable2, and cable3 may be connected to the connector 130, and second ends of the cables cable1, cable2, and cable3 may be connected to the breathing rate sensor 161, the acceleration sensor 162, and the sound sensor 165, respectively. Lengths of the cables cable1, cable2, and cable3 may be freely adjusted.

As shown in FIG. 9A, the electrocardiogram detector 110 may be provided in the patch-type bio-signal monitoring device 100, and at least one of the breathing rate sensor 161, the acceleration sensor 162, and the sound sensor 165 may be provided outside the patch-type bio-signal monitoring device 100.

The patch-type bio-signal monitoring device 100 may be connected to at least one of the breathing rate sensor 161, the acceleration sensor 162, and the sound sensor 165 through the connector 130. The breathing rate sensor 161, the acceleration sensor 162, and the sound sensor 165 may be placed in suitable locations to obtain corresponding biometric sensing signals, and the locations may be changed by the object.

Figure 9B:
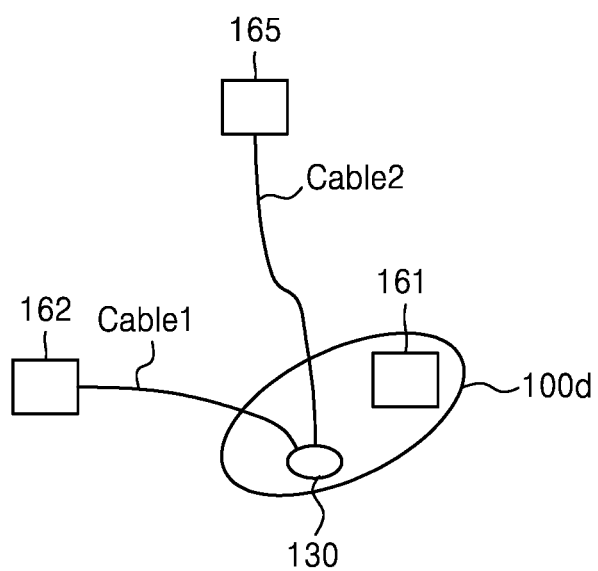
FIG. 9B is a diagram showing an implementation example of a bio-signal monitoring device according to an example embodiment of the present disclosure.
Figure 9C:
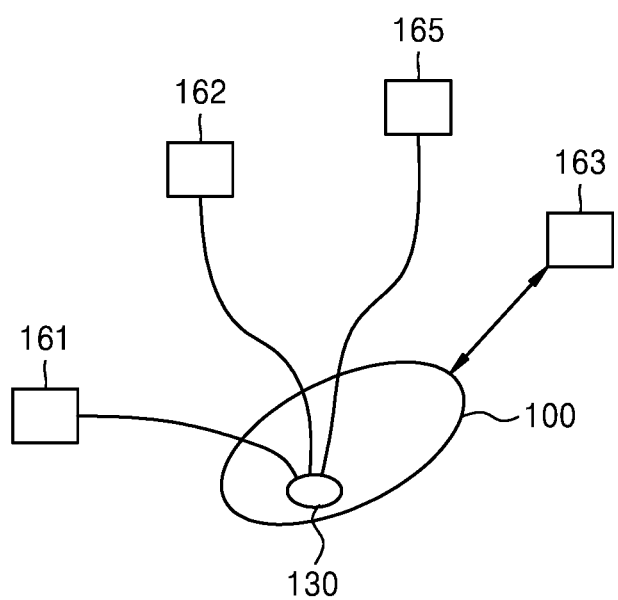
FIG. 9C is a diagram showing an implementation example of a bio-signal monitoring device according to an example embodiment of the present disclosure.

FIG. 9B is a diagram showing an implementation example of a bio-signal monitoring device 100d according to an example embodiment of the present disclosure.

As shown in FIG. 9B, the bio-signal monitoring device 100d may be implemented as a patch-type device and include the electrocardiogram detector 110, the controller 120, the connector 130, and the breathing rate sensor 161 inside the patch-type device. The acceleration sensor 162 or the sound sensor 165 may be provided outside the patch-type device and connected to the connector 130 through cables cable1 and cable2.

FIG. 9C is a diagram showing an implementation example of a bio-signal monitoring device 100e according to an example embodiment of the present disclosure.

Figure 10B:
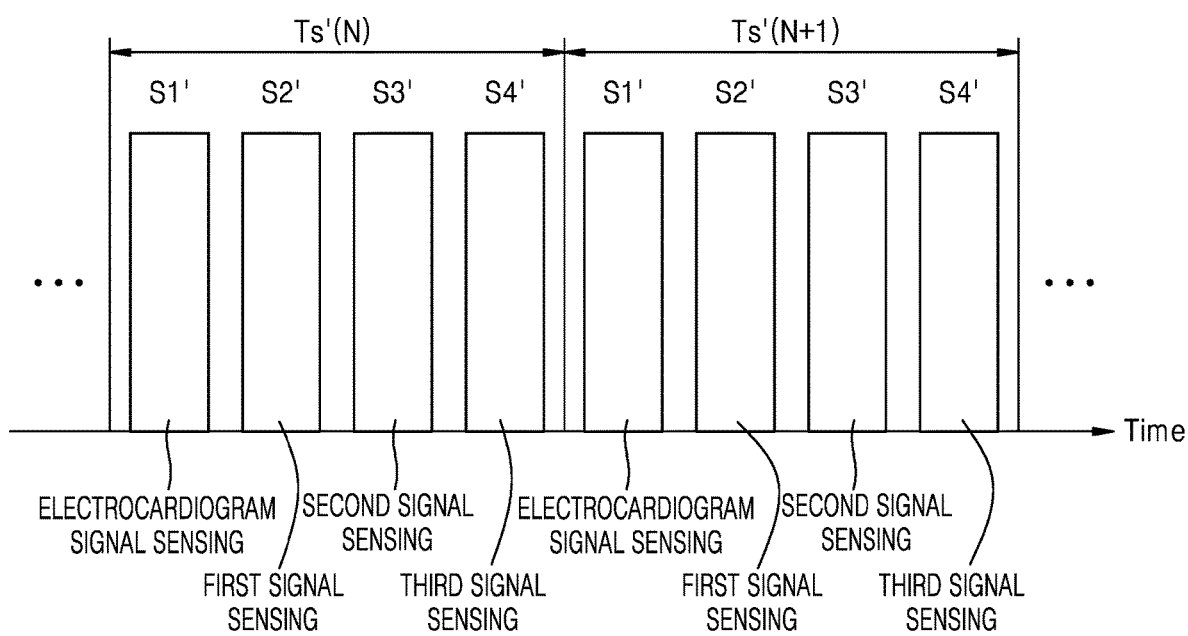
FIG. 10B are a timing diagram showing second method of operating a bio-signal monitoring device according to example embodiments of the present disclosure.

As shown in FIG. 9C, the bio-signal monitoring device 100e may be connected to the breathing rate sensor 161, the acceleration sensor 162, and the sound sensor 165 via wires, may be wirelessly connected to the temperature sensor 163, and may obtain sensing signals. The connector 130 may be implemented to receive various sensing signals through wireless communication. FIGS. 10A and 10B are timing diagrams showing a method of operating a bio-signal monitoring device according to an example embodiment of the present disclosure.

Referring to FIG. 10A, a bio-signal monitoring device 100c may perform electrocardiogram signal processing S1 and breathing rate sensing S2 in a plurality of temporally consecutive sampling periods. The plurality of sampling periods may be constant. The bio-signal monitoring device 100c may perform the electrocardiogram signal processing S1 and the breathing rate sensing S2 in a time division manner during one sampling period. The electrocardiogram signal processing S1 and the breathing rate sensing S2 may be sequentially performed in an N-th sampling period Ts(N) (N is a positive integer equal to or greater than 1), and the electrocardiogram signal processing S1 and the breathing rate sensing S2 may be sequentially performed again in a following (N+1)-th sampling period Ts(N+1). In this regard, the electrocardiogram signal processing S1 and the breathing rate sensing S2 may be repeatedly performed.

Referring to FIG. 10B, the bio-signal monitoring device 100a, 100b, or 100c may perform electrocardiogram signal processing S1', first signal sensing S2', second signal sensing S3', and third signal sensing S4' in a plurality of temporally consecutive sampling periods. The plurality of sampling periods may be constant. The bio-signal monitoring device 100a, 100b, or 100c may perform the electrocardiogram signal processing S1', the first signal sensing S2', the second signal sensing S3' and the third signal sensing S4' in a time division manner during one sampling period. The electrocardiogram signal processing S1', the first signal sensing S2', the second signal sensing S3', and the third signal sensing S4' may be sequentially performed during an N-th sampling period Ts'(N) (N is a positive integer equal to or greater than 1), and the electrocardiogram signal processing S1', the first signal sensing S2', the second signal sensing S3', and the third signal sensing S4' may be sequentially performed again in a following (N+1)-th sampling period Ts'(N+1). In this regard, the electrocardiogram signal processing S1', the first signal sensing S2', the second signal sensing S3', and the third signal sensing S4' may be repeatedly performed. Under the control of the controller 120, at least one of the first signal sensing S2', the second signal sensing S3', and the third signal sensing S4' may be stopped or skipped. At least one of the first signal sensing S2', the second signal sensing S3', and the third signal sensing S4' may not be continuously successively sensed and may be sensed only in a particular period as needed.

The bio-signal monitoring device 100a, 100b, or 100c may allocate repetition periods to electrocardiogram signals, breathing rate sensing signals, acceleration sensing signals, and temperature sensing signals, respectively, thereby successively obtaining electrocardiogram signals, breathing rate sensing signals, acceleration sensing signals, and temperature sensing signals at the repetition periods. Electrocardiogram signals may be obtained 300 times per second at 300 Hz, breathing rate sensing signals may be obtained 10 times per second at 10 Hz, acceleration sensing signals may be obtained 10 times per second at 10 Hz, and temperature sensing signals may be obtained once per 10 seconds at 0.1

Hz. However, the present disclosure is not limited thereto, and sensing signals may be obtained at various repetition periods.

Figure 11:
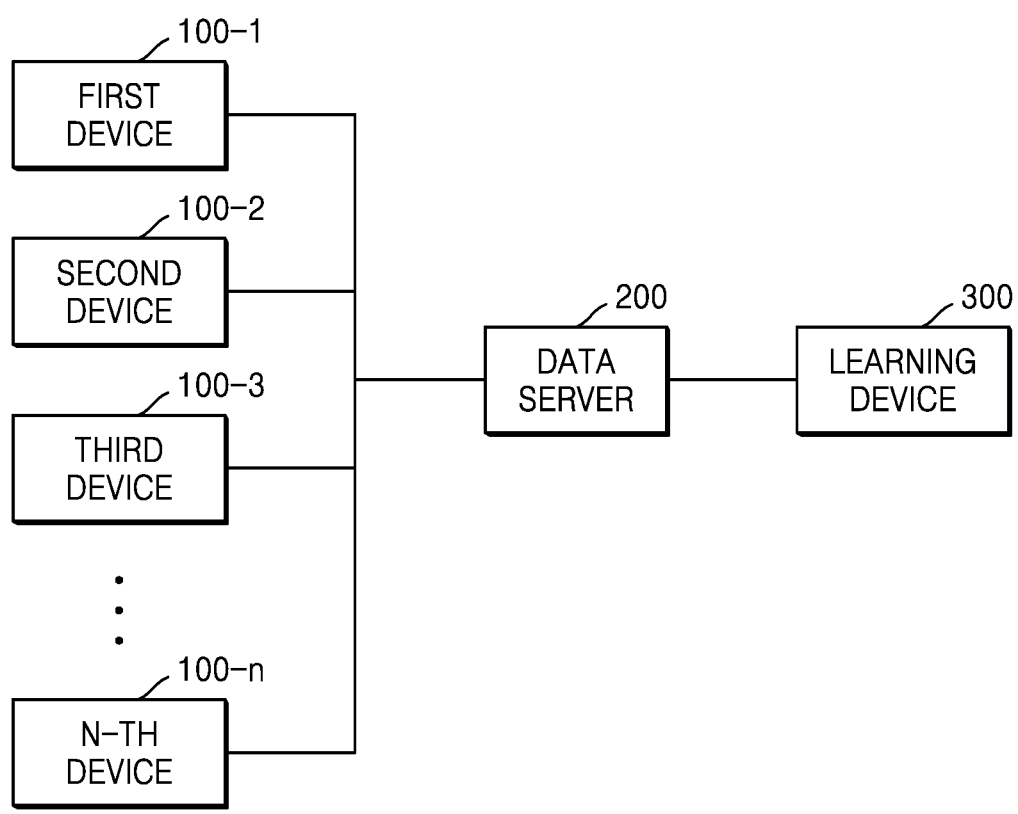
FIG. 11 is a diagram for describing a process of generating a state sensing algorithm.

FIG. 11 is a diagram for describing a process of generating a state sensing algorithm.

A data server 200 receives an electrocardiogram signal and at least one sensing signal from bio-signal monitoring devices 100-1, 100-2, 100-3, . . . , and 100-n and receives health state data detected in relation to received sensing signals.

A learning device 300 may model a state sensing algorithm based on training data that uses an electrocardiogram signal and at least one sensing signal from the data server 200 as inputs and outputs health state data detected in relation to received data. The learning device 300 may generate a model by learning from training data. The state sensing algorithm may be learned by methods such as supervised learning, unsupervised learning, and reinforcement learning. In detail, a state sensing algorithm may be generated by using an algorithm like a decision tree, a Bayesian network, a support vector machine, and an artificial neural network (ANN). From among the above-stated algorithms, an ANN may be classified into a single-layer neural network and a multi-layer neural network according to the number of layers, and a general multi-layer neural network may include an input layer, a hidden layer, and an output layer. The input layer is a layer that receives external data, and the number of neurons in the input layer may be the same as the number of input variables. In other words, in the present disclosure, electrocardiogram detection signals, sensing signals, location information, and time information and health states according to the same are used as input variables. The hidden layer is located between the input layer and the output layer, receives signals from the input layer, extracts features, and transmits the features to the output layer. In the hidden layer, correlations of input variables between input data and output data is trained by using hidden parameters. The output layer receives signals from the hidden layer and outputs the signals to the outside.

The learning apparatus 300 may generate a state sensing algorithm based on training data obtained by further inputting position information and time information in addition to an electrocardiogram signal and at least one sensing signal.

The apparatus described above may be implemented as a hardware component, a software component, and/or a combination of hardware components and software components. For example, the devices and components described in the embodiments may be implemented by using one or more general purpose or special purpose computers, such as a processor, a controller, an arithmetic logic unit (ALU), a digital signal processor, a microcomputer, a field programmable gate array (FPGA). a programmable logic unit (PLU), a microprocessor, or any other device capable of executing and responding to instructions. A processing device may execute an operating system (OS) and one or more software applications running on the OS. The processing device may also access, store, manipulate, process, and generate data in response to execution of software. For the convenience of explanation, it has been described above that one processing device is used. However, it would be obvious to one of ordinary skill in the art that the processing device may include a plurality of processing elements and/or a plurality of types of processing elements. For example, the processing device may include a plurality of processors or one processor and one controller. Also, other processing configurations like parallel processors may be employed.

The software may include a computer program, code, instructions, or a combination of one or more of the foregoing, to configure the processing device to operate as demanded or to command the processing device independently or collectively. For the purpose of interpreting or providing instructions or data to the processing device, software and/or data may be permanently or temporarily embodied in any type of machine, component, physical device, virtual equipment, computer storage medium, or a signal wave to be transmitted. The software may be distributed over networked computer systems so that they may be stored or executed in a distributed manner. The software and data may be stored on one or more computer-readable recording media.

The methods according to embodiments may be embodied in the form of program instructions that can be executed by various computer means and recorded on a computer readable medium. The computer-readable media may include program instructions, data files, and data structures alone or a combination thereof. The program commands recorded on the medium may be specially designed and configured for example embodiments or may be published and available to one of ordinary skill in computer software. Examples of the computer-readable recording medium include a hardware device specially configured to store and perform program instructions, for example, a magnetic medium, such as a hard disk, and a magnetic tape, an optical recording medium, such as a CD-ROM, a DVD, and the like, a magneto-optical medium, such as a floptical disc, ROM, RAM, a flash memory, and the like. Examples of program commands include machine language code such as code generated by a compiler, as well as high-level language code that may be executed by a computer using an interpreter or the like. The hardware device described above may be configured to operate as one or more software modules to perform the operations of the embodiments, and vice versa.

According to a bio-signal monitoring device and a method of monitoring bio-signals according to example embodiments of the present disclosure, a health state and a health risk state of an object may be determined based on a sensing signal from at least one of a breathing rate sensor, an acceleration sensor, and a temperature sensor while sensing an electrocardiogram signal.

Although the embodiments have been described by the limited embodiments and the drawings as described above, various modifications and variations are possible to one of ordinary skill in the art from the above description. For example, the described techniques may be performed in a different order than the described method, and/or components of the described systems, structures, devices, circuits, etc. may be combined or combined in a different manner than the described method, or other components. Or, even if replaced or substituted by equivalents, an appropriate result can be achieved.

Therefore, other implementations, other embodiments, and equivalents of the claims fall within the scope of the claims to be described later.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A bio-signal monitoring device comprising:
   an electrocardiogram detector including at least one electrode, an electrocardiogram signal processing circuit and an electrostatic protection circuit including an electrostatic protection element, wherein a first end of the electrostatic protection element is connected to an input end of the electrostatic protection circuit, wherein the electrocardiogram detector is configured to detect an electrical signal from a heart of an object and output an electrocardiogram signal during an electrocardiogram sensing period; and
   a breathing rate sensor including a respiration rate sensing circuit that is coupled to a second end of the electrostatic protection circuit and processes a signal received from the electrostatic protection circuit to output a capacitance value during a breathing rate sensing period, wherein the breathing rate sensor grounds the second end of the electrostatic protection circuit for the electrocardiogram sensing period, thereby forming a discharge path and protecting the electrostatic protection element;
   wherein the electrostatic protection element includes a diode with a capacitance value and operated as a capacitor;
   a controller coupled to the electrocardiogram detector and the breathing rate sensor;
   a connector configured to:
      be coupled to the breathing rate sensor; and
      transmit, to the controller, a sensing signal including the capacitance value from the breathing rate sensor; and
   a communicator configured to communicate with an external electronic device; and
   a memory that stores executable instructions that, when executed by the controller, facilitate performance of operations, the operations comprising:
      receiving the electrocardiogram signal and generating first analysis data by analyzing the electrocardiogram signal, the first analysis data indicative of a pulse rate of the object, an R-R interval, an interval between specific waveforms, a measurement value of a specific waveform, or a combination thereof;
      receiving a time value of the object;
      receiving the sensing signal from the breathing rate sensor;
      outputting a health state of the object by using a state sensing algorithm learned from training data by a predetermined learning method, wherein the training data employ the electrocardiogram signal, the sensing signal including the capacitance value from the breathing rate sensor and a type of the sensing signal as input data and state data as output data; and
      activating a function of a sound sensor upon determination of the outputted health state of the object and based on the received current location value and the time value of the object;
      controlling the activated function of the sound sensor to detect a voice of the object; and
      transmitting the electrocardiogram signal or the sensing signal to the external electronic device through the communicator,
   wherein the electrocardiogram detector, the breathing rate sensor, the controller, the connector, the communicator, and the memory are implemented in one housing.

2. The bio-signal monitoring device of claim 1, wherein the operations further comprise storing, in an internal memory, the electrocardiogram signal or the sensing signal that is not transmitted to the external electronic device.

3. The bio-signal monitoring device of claim 1, wherein the electrocardiogram signal or the sensing signal is transmitted according to a request signal received from the external electronic device.

4. The bio-signal monitoring device of claim 1, further comprising an acceleration sensor and a temperature sensor coupled to the connector;
   wherein the operations further comprises determining one or more types of sensing signals based on a health state of the object in a previous time period, the received current location value and the received time value and activating or deactivating functions of the acceleration sensor, the temperature sensor or both corresponding to the determined one or more types of sensing signals.

5. The bio-signal monitoring device of claim 4, wherein the connector is designed to be extendable to reach each location of the acceleration sensor, the breathing rate sensor, and the temperature sensor.

6. The bio-signal monitoring device of claim 1, wherein the bio-signal monitoring device includes a patch-type device and the breathing rate sensor is provided externally to the patch-type device via a connection terminal.

7. The bio-signal monitoring device of claim 1, wherein the connector further comprises one or more communication ports.

* * * * *